US012596232B2

(12) United States Patent
Sowards et al.

(10) Patent No.: US 12,596,232 B2
(45) Date of Patent: Apr. 7, 2026

(54) SYSTEMS AND METHODS INCLUDING PROCEDURAL BARRIER-BREACHING CONNECTORS AND CONNECTION-ESTABLISHING DEVICES

(71) Applicant: Bard Access Systems, Inc., Salt Lake City, UT (US)

(72) Inventors: Steffan Sowards, Salt Lake City, UT (US); Anthony K. Misener, Bountiful, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 471 days.

(21) Appl. No.: 17/512,501

(22) Filed: Oct. 27, 2021

(65) Prior Publication Data

US 2022/0128770 A1 Apr. 28, 2022

Related U.S. Application Data

(60) Provisional application No. 63/106,809, filed on Oct. 28, 2020.

(51) Int. Cl.
*G02B 6/38* (2006.01)
*A61B 46/00* (2016.01)

(52) U.S. Cl.
CPC ............ *G02B 6/3817* (2013.01); *A61B 46/00* (2016.02); *G02B 6/3882* (2013.01)

(58) Field of Classification Search
CPC ............................ G02B 6/3817; G02B 6/3882
See application file for complete search history.

(56) References Cited

U.S. PATENT DOCUMENTS

| | | | |
|---|---|---|---|
| 2,831,174 | A | 4/1958 | Hilmo |
| 2,959,766 | A | 11/1960 | Edwin |

(Continued)

FOREIGN PATENT DOCUMENTS

| | | | |
|---|---|---|---|
| EP | 1318576 A1 | 6/2003 | |
| EP | 3270817 A1 | 1/2018 | |

(Continued)

OTHER PUBLICATIONS

"Sampling Accessories" Spectrometers Accessories Catalogue, pp. 71-102, XP055014465, retrieved from the Internet URL: http//www.mikropack.de/d/specto/pdfy-downoads/sampling accessories. pdf, Jan. 1, 2004 (Jan. 1, 2004).

(Continued)

*Primary Examiner* — Uyen Chau N Le
*Assistant Examiner* — Hoang Q Tran
(74) *Attorney, Agent, or Firm* — Rutan & Tucker LLP

(57) ABSTRACT

Procedural barrier-breaching connectors and connection-establishing devices, as well as systems and methods thereof, for establishing portals in procedural barriers are disclosed. For example, a connection-establishing device can include a cap and an extension arm. The cap is configured to sit over a protruding portion of a first medical device with a procedural barrier between the connection-establishing device and the first medical device. The extension arm is configured to push a male connector of a second medical device through the procedural barrier and into a female connector of the first medical device with the extension arm, which establishes one or more functional connections across the procedural barrier between the second medical device and the first medical device. An exemplary method for the connection-establishing device includes a cap-placing step, an articulating step, and a functional connection-establishing (Continued)

step for establishing the one-or-more functional connections.

4 Claims, 11 Drawing Sheets

(56) References Cited

U.S. PATENT DOCUMENTS

| | | | |
|---|---|---|---|
| 3,329,928 A | 7/1967 | Broske | |
| 3,532,095 A | 10/1970 | Miller et al. | |
| 3,597,582 A | 8/1971 | Goode et al. | |
| 3,605,743 A | 9/1971 | Olvera Arce | |
| 3,649,952 A * | 3/1972 | Harmon | H01R 13/637 439/190 |
| 3,665,372 A | 5/1972 | Goode et al. | |
| 3,673,548 A | 6/1972 | Mattingly, Jr. et al. | |
| 3,746,814 A | 7/1973 | Lackey et al. | |
| 3,824,556 A | 7/1974 | Berkovits et al. | |
| 3,842,394 A | 10/1974 | Bolduc | |
| 4,200,348 A | 4/1980 | Stupay | |
| 4,220,387 A | 9/1980 | Biche et al. | |
| 4,254,764 A | 3/1981 | Neward | |
| 4,303,293 A | 12/1981 | Grunwald | |
| 4,369,794 A | 1/1983 | Furler | |
| 4,490,003 A | 12/1984 | Robinson | |
| 4,614,395 A | 9/1986 | Peers-Trevarton | |
| 4,632,121 A | 12/1986 | Johnson et al. | |
| 4,700,997 A | 10/1987 | Strand | |
| 4,702,256 A | 10/1987 | Robinson et al. | |
| 4,761,143 A | 8/1988 | Owens et al. | |
| 4,858,810 A | 8/1989 | Intlekofer et al. | |
| 4,860,742 A | 8/1989 | Park et al. | |
| 4,973,329 A | 11/1990 | Park et al. | |
| 5,159,861 A | 11/1992 | Anderson | |
| 5,178,159 A | 1/1993 | Christian | |
| 5,217,435 A | 6/1993 | Kring | |
| 5,325,746 A | 7/1994 | Anderson | |
| 5,325,868 A | 7/1994 | Kimmelstiel | |
| 5,334,045 A | 8/1994 | Cappa et al. | |
| 5,354,326 A | 10/1994 | Comben et al. | |
| 5,407,368 A | 4/1995 | Strand et al. | |
| 5,423,877 A | 6/1995 | Mackey | |
| 5,437,277 A | 8/1995 | Dumoulin et al. | |
| 5,454,739 A | 10/1995 | Strand | |
| 5,482,038 A | 1/1996 | Ruff | |
| 5,489,225 A | 2/1996 | Julian | |
| 5,501,675 A | 3/1996 | Erskine | |
| 5,538,444 A | 7/1996 | Strand et al. | |
| 5,560,358 A | 10/1996 | Arnold et al. | |
| 5,574,815 A * | 11/1996 | Kneeland | G02B 6/3817 174/75 C |
| 5,591,119 A | 1/1997 | Adair | |
| 5,624,281 A | 4/1997 | Christensson | |
| 5,685,855 A | 11/1997 | Erskine | |
| 5,752,915 A | 5/1998 | Neubauer et al. | |
| 5,766,042 A | 6/1998 | Ries et al. | |
| 5,769,786 A | 6/1998 | Wiegel | |
| 5,792,045 A | 8/1998 | Adair | |
| 5,797,880 A | 8/1998 | Erskine | |
| 5,840,024 A | 11/1998 | Taniguchi et al. | |
| 5,968,082 A | 10/1999 | Heil | |
| 5,975,082 A | 11/1999 | Dowdy | |
| 5,984,918 A | 11/1999 | Garito et al. | |
| 6,050,976 A | 4/2000 | Thorne et al. | |
| 6,090,052 A | 7/2000 | Akerfeldt et al. | |
| 6,102,044 A | 8/2000 | Naidyhorski | |
| 6,132,368 A | 10/2000 | Cooper | |
| 6,140,722 A | 10/2000 | Ballard et al. | |
| 6,162,101 A | 12/2000 | Fischer et al. | |
| 6,319,015 B1 | 11/2001 | Faunce | |
| 6,324,416 B1 | 11/2001 | Seibert | |
| 6,330,480 B1 | 12/2001 | Van der Linden et al. | |
| 6,350,160 B1 | 2/2002 | Feuersanger et al. | |
| 6,415,168 B1 | 7/2002 | Putz | |
| 6,428,336 B1 | 8/2002 | Akerfeldt | |
| 6,546,270 B1 | 4/2003 | Goldin et al. | |
| 6,620,136 B1 | 9/2003 | Pressly, Sr. et al. | |
| 6,663,570 B2 | 12/2003 | Mott et al. | |
| 6,673,078 B1 | 1/2004 | Muncie | |
| 6,714,809 B2 | 3/2004 | Lee et al. | |
| 6,780,065 B2 | 8/2004 | Schwarz | |
| 6,799,991 B2 | 10/2004 | Williams et al. | |
| 6,913,478 B2 | 7/2005 | Lamirey | |
| 7,130,699 B2 | 10/2006 | Huff et al. | |
| 7,144,378 B2 | 12/2006 | Arnott | |
| 7,255,609 B1 | 8/2007 | Epstein | |
| 7,274,956 B2 | 9/2007 | Mott et al. | |
| 7,402,083 B2 | 7/2008 | Kast et al. | |
| 7,452,360 B2 | 11/2008 | Trudeau et al. | |
| 7,553,193 B2 | 6/2009 | Kast et al. | |
| 7,585,118 B1 * | 9/2009 | Lumpkin | G02B 6/3825 385/88 |
| 7,633,023 B1 | 12/2009 | Cappa et al. | |
| 7,666,191 B2 | 2/2010 | Orban, III et al. | |
| 7,753,696 B2 | 7/2010 | Hoecke et al. | |
| 7,771,394 B2 | 8/2010 | Shue et al. | |
| 7,819,844 B2 | 10/2010 | Spenser et al. | |
| 7,972,282 B2 | 7/2011 | Clark et al. | |
| 8,105,338 B2 | 1/2012 | Anderson et al. | |
| 8,147,275 B1 | 4/2012 | Drake et al. | |
| 8,206,175 B2 | 6/2012 | Boyd et al. | |
| 8,267,873 B2 | 9/2012 | Yanuma | |
| 8,388,541 B2 | 3/2013 | Messerly et al. | |
| 8,480,427 B2 | 7/2013 | Marshalok | |
| 8,548,601 B2 | 10/2013 | Chinn et al. | |
| 8,597,042 B2 | 12/2013 | King | |
| 8,603,011 B2 | 12/2013 | Landowski | |
| 8,620,412 B2 | 12/2013 | Griffiths et al. | |
| 8,639,340 B2 | 1/2014 | Sommer et al. | |
| 8,666,510 B2 | 3/2014 | Chinn et al. | |
| 8,781,555 B2 | 7/2014 | Burnside et al. | |
| 8,849,382 B2 | 9/2014 | Cox et al. | |
| 8,869,887 B2 | 10/2014 | Deere et al. | |
| 8,932,258 B2 | 1/2015 | Blanchard et al. | |
| 8,958,878 B2 | 2/2015 | Cejnar | |
| 9,059,548 B2 | 6/2015 | Stump et al. | |
| 9,095,680 B2 | 8/2015 | Steegers et al. | |
| 9,101,775 B2 | 8/2015 | Barker | |
| 9,107,594 B2 | 8/2015 | Selvitelli et al. | |
| 9,108,027 B2 | 8/2015 | Eubanks et al. | |
| 9,131,956 B2 | 9/2015 | Shaughnessy et al. | |
| 9,144,395 B2 | 9/2015 | Sela et al. | |
| 9,425,537 B2 | 8/2016 | Barker | |
| 9,456,766 B2 | 10/2016 | Cox et al. | |
| 9,492,097 B2 | 11/2016 | Wilkes et al. | |
| 9,521,961 B2 | 12/2016 | Silverstein et al. | |
| 9,526,440 B2 | 12/2016 | Burnside et al. | |
| 9,549,685 B2 | 1/2017 | Cox et al. | |
| 9,554,716 B2 | 1/2017 | Burnside et al. | |
| 9,636,031 B2 | 5/2017 | Cox | |
| 9,649,048 B2 | 5/2017 | Cox et al. | |
| 9,656,093 B2 | 5/2017 | Villarta et al. | |
| 9,662,506 B2 | 5/2017 | Govea | |
| 9,675,784 B2 | 6/2017 | Belson | |
| 9,681,823 B2 | 6/2017 | Messerly et al. | |
| 9,808,647 B2 | 11/2017 | Rhodes et al. | |
| 9,872,971 B2 | 1/2018 | Blanchard | |
| 9,919,145 B2 | 3/2018 | Bondhus et al. | |
| 9,950,139 B2 | 4/2018 | Blanchard et al. | |
| 9,999,371 B2 | 6/2018 | Messerly et al. | |
| 10,105,121 B2 | 10/2018 | Burnside et al. | |
| 10,130,806 B2 | 11/2018 | Leven et al. | |
| 10,165,962 B2 | 1/2019 | Messerly et al. | |
| 10,201,713 B2 | 2/2019 | Leven | |
| 10,231,753 B2 | 3/2019 | Burnside et al. | |
| 10,238,418 B2 | 3/2019 | Cox et al. | |
| 10,238,880 B2 | 3/2019 | Thom et al. | |
| 10,307,602 B2 | 6/2019 | Leven | |
| 10,322,253 B2 | 6/2019 | Einav et al. | |
| 10,342,575 B2 | 7/2019 | Cox et al. | |
| 10,449,330 B2 | 10/2019 | Newman et al. | |
| 10,524,691 B2 | 1/2020 | Newman et al. | |
| 10,602,958 B2 | 3/2020 | Silverstein et al. | |
| 10,751,509 B2 | 8/2020 | Misener | |

(56) References Cited

U.S. PATENT DOCUMENTS

| | | | |
|---|---|---|---|
| 10,772,696 | B2 | 9/2020 | Thompson et al. |
| 10,849,695 | B2 | 12/2020 | Cox et al. |
| 10,992,078 | B2 | 4/2021 | Thompson et al. |
| D921,884 | S | 6/2021 | Tran et al. |
| 11,474,310 | B2 | 10/2022 | Sowards et al. |
| 2002/0197905 | A1 | 12/2002 | Kaufmann et al. |
| 2003/0199827 | A1 | 10/2003 | Thorne |
| 2003/0216723 | A1 | 11/2003 | Shinmura et al. |
| 2004/0039372 | A1 | 2/2004 | Carmody |
| 2004/0146252 | A1 | 7/2004 | Healy et al. |
| 2005/0177199 | A1 | 8/2005 | Hansen et al. |
| 2005/0283216 | A1 | 12/2005 | Pyles |
| 2006/0025677 | A1 | 2/2006 | Verard et al. |
| 2006/0030864 | A1 | 2/2006 | Kennedy et al. |
| 2006/0161138 | A1 | 7/2006 | Orban et al. |
| 2006/0173407 | A1 | 8/2006 | Shaughnessy et al. |
| 2007/0062544 | A1 | 3/2007 | Rauk Bergstrom et al. |
| 2007/0118079 | A1 | 5/2007 | Moberg et al. |
| 2007/0160327 | A1 | 7/2007 | Lewallen et al. |
| 2007/0161969 | A1 | 7/2007 | Andersen |
| 2007/0293719 | A1 | 12/2007 | Scopton et al. |
| 2008/0009720 | A1 | 1/2008 | Schefelker et al. |
| 2008/0046062 | A1 | 2/2008 | Camps et al. |
| 2008/0177361 | A1 | 7/2008 | Anderson |
| 2008/0236598 | A1 | 10/2008 | Gobel |
| 2008/0287876 | A1 | 11/2008 | Shue et al. |
| 2008/0304793 | A1 | 12/2008 | Benaron et al. |
| 2009/0156926 | A1 | 6/2009 | Messerly et al. |
| 2009/0234328 | A1 | 9/2009 | Cox et al. |
| 2010/0036227 | A1 | 2/2010 | Cox et al. |
| 2010/0139669 | A1 | 6/2010 | Piferi et al. |
| 2010/0204569 | A1 | 8/2010 | Burnside et al. |
| 2010/0300459 | A1 | 12/2010 | Lair |
| 2011/0160824 | A1 | 6/2011 | Ware et al. |
| 2011/0166528 | A1 | 7/2011 | Millerd et al. |
| 2011/0250775 | A1 | 10/2011 | Bies et al. |
| 2011/0257503 | A1 | 10/2011 | Mehdizadeh et al. |
| 2012/0071752 | A1 | 3/2012 | Sewell et al. |
| 2012/0253320 | A1 | 10/2012 | Steegers et al. |
| 2013/0023729 | A1 | 1/2013 | Vazales et al. |
| 2013/0095689 | A1 | 4/2013 | Hayman et al. |
| 2013/0104884 | A1 | 5/2013 | Vazales et al. |
| 2013/0109980 | A1 | 5/2013 | Teo |
| 2013/0211225 | A1 | 8/2013 | Zhang |
| 2013/0245640 | A1 | 9/2013 | Whitmore, III |
| 2013/0247921 | A1 | 9/2013 | Dye et al. |
| 2013/0269713 | A1 | 10/2013 | Bui et al. |
| 2013/0289417 | A1 | 10/2013 | Grunwald et al. |
| 2013/0308137 | A1 | 11/2013 | Manzke et al. |
| 2013/0317356 | A1 | 11/2013 | Ramachandran et al. |
| 2013/0331688 | A1 | 12/2013 | Heigl et al. |
| 2013/0337674 | A1 | 12/2013 | Stump et al. |
| 2014/0150782 | A1 | 6/2014 | Vazales et al. |
| 2015/0012072 | A1 | 1/2015 | Johnson et al. |
| 2015/0031987 | A1 | 1/2015 | Pameijer et al. |
| 2015/0105654 | A1 | 4/2015 | Meyer |
| 2015/0144514 | A1 | 5/2015 | Brennan et al. |
| 2015/0148615 | A1 | 5/2015 | Brennan et al. |
| 2015/0164583 | A1 | 6/2015 | Zarins et al. |
| 2015/0177467 | A1* | 6/2015 | Gniadek ............... H01R 13/625 |
| | | | 439/365 |
| 2015/0190615 | A1 | 7/2015 | Shaltis |
| 2015/0223897 | A1 | 8/2015 | Kostrzewski et al. |
| 2015/0305816 | A1 | 10/2015 | Hadzic |
| 2016/0018602 | A1 | 1/2016 | Govari et al. |
| 2016/0158499 | A1 | 6/2016 | Helm |
| 2016/0213432 | A1 | 7/2016 | Flexman et al. |
| 2017/0014194 | A1 | 1/2017 | Duindam et al. |
| 2017/0181646 | A1 | 6/2017 | Hayes et al. |
| 2017/0231700 | A1 | 8/2017 | Cox et al. |
| 2017/0261699 | A1 | 9/2017 | Compton et al. |
| 2017/0296284 | A1 | 10/2017 | Turturro et al. |
| 2017/0333136 | A1 | 11/2017 | Hladio et al. |
| 2018/0071509 | A1 | 3/2018 | Tran et al. |
| 2018/0110951 | A2 | 4/2018 | Beard |
| 2018/0140170 | A1 | 5/2018 | Van Putten et al. |
| 2018/0289927 | A1 | 10/2018 | Messerly |
| 2019/0069877 | A1 | 3/2019 | Burnside et al. |
| 2019/0180647 | A1 | 6/2019 | Fujiki |
| 2019/0231172 | A1 | 8/2019 | Barron et al. |
| 2019/0237902 | A1 | 8/2019 | Thompson et al. |
| 2019/0350621 | A1* | 11/2019 | Zitnick .............. A61B 17/3423 |
| 2019/0350663 | A1 | 11/2019 | Thompson et al. |
| 2020/0221934 | A1 | 7/2020 | Van Der Mark et al. |
| 2020/0330173 | A1 | 10/2020 | Kapadia et al. |
| 2020/0345441 | A1 | 11/2020 | Thompson et al. |
| 2021/0030504 | A1 | 2/2021 | Thompson et al. |
| 2021/0038322 | A1 | 2/2021 | Thompson et al. |
| 2021/0298680 | A1 | 9/2021 | Sowards et al. |
| 2021/0307856 | A1 | 10/2021 | Aguirre |
| 2022/0110707 | A1 | 4/2022 | Sowards et al. |
| 2022/0110708 | A1 | 4/2022 | Misener et al. |
| 2022/0241044 | A1 | 8/2022 | Thompson et al. |
| 2023/0248459 | A1 | 8/2023 | Thompson et al. |
| 2024/0350206 | A1 | 10/2024 | Thompson et al. |
| 2024/0366330 | A1 | 11/2024 | Thompson et al. |
| 2025/0192473 | A1 | 6/2025 | Thompson et al. |

FOREIGN PATENT DOCUMENTS

| | | | |
|---|---|---|---|
| EP | 3673801 | A1 | 7/2020 |
| WO | 9413201 | A1 | 6/1994 |
| WO | 9619017 | A1 | 6/1996 |
| WO | 9822180 | A1 | 5/1998 |
| WO | 2004101068 | A1 | 11/2004 |
| WO | 2005044332 | A2 | 5/2005 |
| WO | 2005072807 | A1 | 8/2005 |
| WO | 2005077453 | A2 | 8/2005 |
| WO | 2007058816 | A2 | 5/2007 |
| WO | 2007109285 | A2 | 9/2007 |
| WO | 2007149618 | A2 | 12/2007 |
| WO | 2009050599 | A2 | 4/2009 |
| WO | 2010123701 | A1 | 10/2010 |
| WO | 2011033107 | A1 | 3/2011 |
| WO | 2011082160 | A2 | 7/2011 |
| WO | 2012102745 | A2 | 8/2012 |
| WO | 2015075002 | A1 | 5/2015 |
| WO | 2016146993 | A1 | 9/2016 |
| WO | 2019/148201 | A1 | 8/2019 |
| WO | 2019/165011 | A1 | 8/2019 |
| WO | 2019/221926 | A1 | 11/2019 |
| WO | 2021021408 | A1 | 2/2021 |
| WO | 2021026502 | A1 | 2/2021 |
| WO | 2022081583 | A1 | 4/2022 |
| WO | 2022081591 | A1 | 4/2022 |
| WO | 2022093991 | A1 | 5/2022 |

OTHER PUBLICATIONS

PCT/US2021/054593 filed Oct. 12, 2021 International Search Report and Written Opinion dated Jan. 24, 2022.

PCT/US2021/054607 filed Oct. 12, 2021 International Search Report and Written Opinion dated Jan. 21, 2022.

PCT/US2021/056896 filed Oct. 27, 2021 International Search Report and Written Opinion dated Mar. 22, 2022.

U.S. Appl. No. 16/281,079, filed Feb. 20, 2019 Examiner's Answer dated Feb. 25, 2022.

PCT/US2019/015710 filed Jan. 29, 2019 International Preliminary Report on Patentability dated Apr. 29, 2019.

PCT/US2019/015710 filed Jan. 29, 2019 International Search Report and Written Opinion dated Apr. 29, 2019.

PCT/US2019/018851 filed Feb. 20, 2019 Internation Search Report and Written Opinion dated May 7, 2019.

PCT/US2019/018851 filed Feb. 20, 2019 International Preliminary Report on Patentability dated May 7, 2019.

PCT/US2020/41267 filed Jul. 8, 2020 Internation Search Report and Written Opinion dated Oct. 1, 2020.

PCT/US2020/45498 filed Aug. 7, 2020 International Search Report and Written Opinion dated Oct. 4, 2020.

U.S. Appl. No. 12/426,175, filed Apr. 17, 2009 Advisory Action dated Nov. 26, 2013.

(56) References Cited

OTHER PUBLICATIONS

U.S. Appl. No. 12/426,175, filed Apr. 17, 2009 Decision on Appeal dated Nov. 7, 2016.
U.S. Appl. No. 12/426,175, filed Apr. 17, 2009 Examiner's Answer dated Oct. 7, 2014.
U.S. Appl. No. 12/426,175, filed Apr. 17, 2009 Final Office Action dated Aug. 2, 2013.
U.S. Appl. No. 12/426,175, filed Apr. 17, 2009 Final Office Action dated Jan. 31, 2014.
U.S. Appl. No. 12/426,175, filed Apr. 17, 2009 Non-Final Office Action dated Dec. 3, 2012.
U.S. Appl. No. 12/426,175, filed Apr. 17, 2009 Notice of Allowance dated Dec. 13, 2016.
U.S. Appl. No. 12/715,556, filed Mar. 2, 2010 Final Office Action dated Oct. 2, 2013.
U.S. Appl. No. 12/715,556, filed Mar. 2, 2010 Non-Final Office Action dated Sep. 13, 2012.
U.S. Appl. No. 15/585,051, filed May 2, 2017 Examiner's Answer dated May 2, 2019.
U.S. Appl. No. 15/585,051, filed May 2, 2017 Final Office Action dated Feb. 28, 2018.
U.S. Appl. No. 15/585,051, filed May 2, 2017 Final Office Action dated Mar. 15, 2018.
U.S. Appl. No. 15/585,051, filed May 2, 2017 Non-Final Office Action dated Jul. 14, 2017.
U.S. Appl. No. 16/261,368, filed Jan. 29, 2019 Advisory Action dated Jul. 21, 2020.
U.S. Appl. No. 16/261,368, filed Jan. 29, 2019 Non-Final Office Action dated Jan. 23, 2020.
U.S. Appl. No. 16/261,368, filed Jan. 29, 2019 Notice of Allowance dated Jan. 15, 2021.
U.S. Appl. No. 16/281,079, filed Feb. 20, 2019 Final Office Action dated Aug. 25, 2020.
U.S. Appl. No. 16/281,079, filed Feb. 20, 2019 Non-Final Office Action dated Apr. 1, 2020.
U.S. Appl. No. 16/281,079, filed Feb. 20, 2019 Non-Final Office Action dated Apr. 20, 2021.
U.S. Appl. No. 16/402,074, filed May 2, 2019 Non-Final Office Action dated Apr. 16, 2020.
U.S. Appl. No. 16/932,425, filed Jul. 17, 2020 Non-Final Office Action dated Jun. 18, 2021.
U.S. Appl. No. 16/932,425, filed Jul. 17, 2020 Notice of Allowance dated Jan. 10, 2022.

Design U.S. Appl. No. 29/658,136 Specification and Drawings filed Jul. 27, 2018.
PCT/US19/30470 filed May 2, 2019 International Search Report and Written Opinion dated Jul. 19, 2019.
U.S. Appl. No. 16/923,912, filed Jul. 8, 2020 Notice of Allowance dated Mar. 27, 2023.
U.S. Appl. No. 16/988,452, filed Aug. 7, 2020 Non-Final Office Action dated Mar. 16, 2023.
U.S. Appl. No. 17/723,246, filed Apr. 18, 2022, Non-Final Office Action dated Sep. 27, 2022.
U.S. Appl. No. 17/723,246, filed Apr. 18, 2022, Notice of Allowance dated Jan. 27, 2023.
U.S. Appl. No. 17/499,635, filed Oct. 12, 2021 Non-Final Office Action dated Dec. 4, 2024.
U.S. Appl. No. 18/539,518, filed Dec. 14, 2023, Notice of Allowance dated Nov. 7, 2024.
U.S. Appl. No. 16/988,452, filed Aug. 7, 2020 Advisory Action dated Oct. 2, 2023.
U.S. Appl. No. 16/988,452, filed Aug. 7, 2020 Non-Final Office Action dated Nov. 9, 2023.
U.S. Appl. No. 17/240,826, filed Apr. 26, 2021 Notice of Allowance dated Nov. 9, 2023.
U.S. Appl. No. 17/499,635, filed Oct. 12, 2021 Advisory Action dated Aug. 8, 2025.
U.S. Appl. No. 17/499,635, filed Oct. 12, 2021 Final Office Action dated May 19, 2025.
U.S. Appl. No. 17/499,688, filed Oct. 12, 2021 Non-Final Office Action dated Jul. 30, 2025.
U.S. Appl. No. 18/761,182, filed Jul. 1, 2024 Non-Final Office Action dated Jun. 20, 2025.
EP 20849119.1 filed Mar. 4, 2022 Extended European Search Report dated Jun. 26, 2023.
U.S. Appl. No. 16/988,452, filed Aug. 7, 2020 Final Office Action dated Mar. 16, 2023.
U.S. Appl. No. 17/240,826, filed Apr. 26, 2021, Non-Final Office Action dated Jul. 19, 2023.
U.S. Appl. No. 17/499,635, filed Oct. 12, 2021 Non-Final Office Action dated Aug. 21, 2025.
U.S. Appl. No. 18/761,182, filed Jul. 1, 2024 Notice of Allowance dated Oct. 23, 2025.
U.S. Appl. No. 18/773,870, filed Jul. 16, 2024 Non-Final Office Action dated Sep. 23, 2025.

* cited by examiner

SYSTEMS AND METHODS INCLUDING
PROCEDURAL BARRIER-BREACHING
CONNECTORS AND
CONNECTION-ESTABLISHING DEVICES

PRIORITY

This application claims the benefit of priority to U.S.
Provisional Application No. 63/106,809, filed Oct. 28, 2020,
which is incorporated by reference in its entirety into this
application.

BACKGROUND

Procedural fields are typically established about patients
with one or more procedural barriers before medical proce-
dures. For example, sterile fields can be established over or
around patients by covering the patients with sterile drapes.
Oftentimes, the medical procedures require multiple-use
medical devices that cannot be sterilized, which mandate
placement of such medical devices under the sterile drapes;
however, sterile single-use medical devices often need to be
functionally connected to the multiple-use medical devices.
Some existing solutions rely on arbitrarily breaching sterile
drapes to make functional connections between sterile
single-use medical devices and multiple-use medical
devices. But arbitrarily breaching such sterile drapes risks
contaminating the sterile fields carefully established about
the patients. That, and establishing some functional connec-
tions such as optical connections between the sterile single-
use medical devices and the multiple-use medical devices
can be difficult, particularly through arbitrary, self-made
breaches in the sterile drapes. What is needed are procedural
barrier-breaching connectors and connection-establishing
devices for establishing safe, routine, functional connections
between sterile single-use medical devices and multiple-use
medical devices.

Disclosed herein are procedural barrier-breaching con-
nectors and connection-establishing devices, as well as
systems and methods thereof, for establishing portals in
procedural barriers.

SUMMARY

Disclosed herein is a connection system including, in
some embodiments, a male connector and a female connec-
tor. The male connector includes a base, external threads
around the base, and opposing wings about a portion of the
base. The base includes a longitudinal through hole having
a terminal opening configured for holding therein a ferrule
including an optical fiber. The wings are opposite the
terminal opening. The wings are configured for turning the
male connector by hand along a longitudinal axis thereof.
The female connector includes a receptacle and internal
threads around the receptacle. The receptacle includes a
longitudinal through hole having an internal opening con-
figured for holding therein another ferrule including another
optical fiber. The internal threads around the receptacle are
complementary with the external threads of the male con-
nector. The male and female connectors are configured to
establish an optical connection between the optical fiber of
the male connector and the other optical fiber of the female
connector when the optical fiber and the other optical fiber
are respectively held in the male connector and the female
connector.

In some embodiments, the external threads around the
base of the male connector and the internal threads around the receptacle of the female connector are electrically con-
ductive. The male and female connectors are configured to
establish an electrical connection between a conductive wire
of the male connector and another conductive wire of the
female connector when the conductive wire and the other
conductive wire are respectively held in the male connector
and the female connector and connected to the internal
threads and the external threads.

In some embodiments, the external threads around the
base of the male connector include a cutting edge configured
to cut through a procedural barrier when the male connector
is placed against the procedural barrier and turned by hand
along the longitudinal axis thereof.

In some embodiments, the base of the male connector and
the receptacle of the female connector are complementarily
tapered.

Also disclosed herein is a connection system including, in
some embodiments, a male connector and a female connec-
tor. The male connector includes two or more prongs and an
optical-fiber holder. The two-or-more prongs extend to a
common terminal end of the male connector. The optical-
fiber holder is along a longitudinal axis of the male connec-
tor between the two-or-more prongs and short of the com-
mon terminal end. The optical-fiber holder is configured for
holding therein a ferrule including an optical fiber. The
female connector includes two or more prong receptacles
and an optical-fiber receptacle. The two-or-more prong
receptacles correspond in number to the two-or-more prongs
and extend to a common terminal end of the female con-
nector. The optical-fiber receptacle is along a longitudinal
axis of the female connector between the two-or-more prong
receptacles and commensurate with the common terminal
end of the female connector. The optical-fiber receptacle is
configured for holding therein another ferrule including
another optical fiber. The male and female connectors are
configured to establish an optical connection between the
optical fiber of the male connector and the other optical fiber
of the female connector when the optical fiber and the other
optical fiber are respectively held in the male connector and
the female connector.

In some embodiments, the two-or-more prongs of the
male connector and two or more contacts respectively
disposed within the two-or-more prong receptacles of the
female connector are electrically conductive. The male and
female connectors are configured to establish an electrical
connection between a conductive wire of the male connector
and another conductive wire of the female connector when
the conductive wire and the other conductive wire are
respectively coupled to the two-or-more prongs in the male
connector and the two-or-more contacts in female connector.

In some embodiments, each prong of the two-or-more
prongs of the male connector include a cutting edge con-
figured to cut through a procedural barrier when the male
connector is placed against the procedural barrier and
pushed by hand therethrough.

Also disclosed herein is a connection system including a
male connector and a female connector. The male connector
includes a sleeve, a cutting edge around a major opening of
the sleeve, and a holed stopper. The sleeve has a through
hole configured to allow a cable including an optical fiber to
be slidably disposed therein. The cutting edge is opposite the
through hole. The cutting edge is configured to cut through
a procedural barrier when the sleeve is placed against the
procedural barrier and turned by hand along a longitudinal
axis of the sleeve. The holed stopper is configured to be
disposed over the cable or a ferrule around the optical fiber.
The holed stopper is configured to stop the cable from slipping though the through hole. The female connector includes an optical-fiber receptacle. The optical-fiber receptacle includes a longitudinal through hole having an internal opening configured for holding therein another ferrule including another optical fiber. The male and female connectors are configured to establish an optical connection between the optical fiber of the male connector and the other optical fiber of the female connector when the optical fiber and the other optical fiber are respectively held in the male connector and the female connector.

In some embodiments, the sleeve of the male connector has internal threads around an inside of the sleeve and the female connector has complementary external threads around an outside of the optical-fiber receptacle. The internal threads of the male connector and the external threads of the female connector are configured for screwing together the male connector and the female connector.

Also disclosed herein is a connection system including a male connector and a female connector. The male connector includes a head, a splittable shank extending from the head, and a spiral cutting edge around the splittable shank. The head has a through hole configured to allow a cable including an optical fiber to be slidably disposed therein. The splittable shank is configured to split along its length to allow a ferrule including the optical fiber of the cable to be pushed past a terminal end of the male connector. The spiral cutting edge is configured to cut through a procedural barrier when the male connector is placed against the procedural barrier and turned by hand along the longitudinal axis thereof. The female connector includes an optical-fiber receptacle. The optical-fiber receptacle includes a longitudinal through hole having an internal opening configured for holding therein another ferrule including another optical fiber. The male and female connectors are configured to establish an optical connection between the optical fiber of the male connector and the other optical fiber of the female connector when the optical fiber and the other optical fiber are respectively held in the male connector and the female connector.

In some embodiments, the splittable shank is configured to split in the optical-fiber receptacle to allow the ferrule including the optical fiber of the cable to be pushed past the terminal end of the male connector.

Also disclosed herein is a connection-establishing device including, in some embodiments, a cap and an extension arm. The cap is configured to sit over a protruding portion of a first medical device with a procedural barrier between the connection-establishing device and the first medical device. The extension arm is coupled by a hinge pin to the cap. The extension arm is configured to push a male connector of a second medical device through the procedural barrier and into a female connector of the first medical device by articulating the extension arm and establishing one or more functional connections across the procedural barrier between the second medical device on a clinician-facing side of the procedural barrier and the first medical device on a patient-facing side of the procedural barrier.

Also disclosed herein is a connection-establishing device including, in some embodiments, a cap, bail wire coupled to the cap, and an extension arm coupled to the cap. The cap is configured to sit over a protruding portion of a first medical device with a procedural barrier between the connection-establishing device and the first medical device. The bail wire is coupled to the cap by ends of the bail wire in bores of the cap. The bail wire is configured to secure the cap over the protruding portion of the first medical device by way of a hinge mechanism. The extension arm is coupled by a hinge pin to the cap. The extension arm is configured to push a male connector of a second medical device through the procedural barrier and into a female connector of the first medical device by articulating the extension arm. The extension arm is thusly configured to establish one or more functional connections across the procedural barrier between the second medical device on a clinician-facing side of the procedural barrier and the first medical device on a patient-facing side of the procedural barrier.

Also disclosed herein is a method of a connection system including a connector-placing step, a connector-turning step, and optical connection-establishing step. The connector-placing step includes placing a bottom portion of a base of a male connector into a top portion of a receptacle of a female connector with a procedural barrier therebetween. The connector-turning step includes turning the male connector by hand along a longitudinal axis thereof by way of opposing wings about a portion of the base opposite the bottom portion of the base while placing the male connector against the procedural drape. The connector-turning step also includes cutting through the procedural barrier with external threads around the base of the male connector having a cutting edge. The optical connection-establishing step includes establishing an optical connection between an optical fiber disposed in a terminal opening in the bottom portion of the male connector and another optical fiber disposed in an internal opening of the female connector respectively held in the male connector and the female connector.

In some embodiments, the method further includes an electrical connection-establishing step. The electrical connection-establishing step includes establishing an electrical connection between a conductive wire of the male connector and another conductive wire of the female connector. The conductive wire and the other conductive wire are respectively connected to the external threads of the male connector and complementary internal threads around the receptacle of the female connector.

Also disclosed herein is a method of a connection system including, in some embodiments, a connector-placing step, a connector-pushing step, and an optical connection-establishing step. The connector-placing step includes placing two or more prongs of a male connector against a procedural barrier. The connector-pushing step includes pushing the two-or-more prongs through the procedural barrier into two or more prong receptacles of a female connector corresponding in number to the two-or-more prongs of the male connector. The connector-pushing step also includes cutting through the procedural barrier with a cutting edge of each prong of the two-or-more prongs of the male connector. The optical connection-establishing step includes establishing an optical connection between an optical fiber disposed in an optical-fiber holder along a longitudinal axis of the male connector between the two-or-more prongs and another optical fiber disposed in an optical-fiber receptacle along a longitudinal axis of the female connector between the two-or-more prong receptacles.

In some embodiments, the method further includes an electrical connection-establishing step. The electrical connection-establishing step includes establishing an electrical connection between a conductive wire coupled to the two-or-more prongs of the male connector and another conductive wire coupled to two or more contacts respectively disposed within the two-or-more prong receptacles of the female connector.

Also disclosed herein is a method of a connection system including, in some embodiments, a connector-placing step, a connector-turning step, and a cable-sliding step. The connector-placing step includes placing a bottom portion of a sleeve of a male connector over a top portion of a receptacle of a female connector with a procedural barrier therebetween. The connector-turning step includes turning the male connector by hand along a longitudinal axis of the sleeve while placing the male connector against the procedural drape. The connector-turning step also includes cutting through the procedural barrier with a cutting edge around a major opening of the sleeve opposite a through hole. The cable-sliding step includes sliding a cable including an optical fiber through a through hole opposite the bottom portion of the sleeve of the male connector into the receptacle of the female connector. The cable-sliding step also includes establishing an optical connection between the optical fiber and another optical fiber disposed in the receptacle of the female connector.

In some embodiments, the sleeve of the male connector has internal threads around an inside of the sleeve and the female connector has complementary external threads around an outside of the optical-fiber receptacle for screwing together the male connector and the female connector subsequent to cutting the procedural drape in the connector-turning step.

Also disclosed herein is a method of a connection system including, in some embodiments, a connector-placing step, a connector-turning step, a connector-inserting step, and a cable-sliding step. The connector-placing step includes placing a spiral cutting edge of a splittable shank of a male connector over a longitudinal through hole of a receptacle of a female connector with a procedural barrier therebetween. The connector-turning step includes turning the male connector by hand along a longitudinal axis thereof while placing the male connector against the procedural drape. The connector-turning step also includes cutting through the procedural barrier with the cutting edge of the splittable shank. The connector-inserting step includes inserting the splittable shank into the longitudinal through hole of the receptacle of the female connector and splitting the splittable shank along its length. The cable-sliding step includes sliding a cable including an optical fiber through a through hole in a head of the male connector opposite the splittable shank into the receptacle of the female connector. The cable-sliding step also includes establishing an optical connection between the optical fiber and another optical fiber disposed in the receptacle of the female connector.

Also disclosed herein is a method of a connection-establishing device including, in some embodiments, a cap-placing step, an articulating step, and a functional connection-establishing step. The cap-placing step includes placing a cap over a protruding portion of a first medical device with a procedural barrier between the connection-establishing device and the first medical device. The articulating step includes articulating an extension arm coupled by a hinge pin to the cap to push a male connector of a second medical device through the procedural barrier and into a female connector of the first medical device. The functional connection-establishing step includes establishing one or more functional connections across the procedural barrier between the second medical device on a clinician-facing side of the procedural barrier and the first medical device on a patient-facing side of the procedural barrier.

Also disclosed herein is a method of a connection-establishing device including, in some embodiments, a cap-placing step, a securing step, an articulating step, and a functional connection-establishing step. The cap-placing step includes placing a cap over a protruding portion of a first medical device with a procedural barrier between the connection-establishing device and the first medical device. The securing step includes securing the cap over the protruding portion of the first medical device by way of a hinge mechanism of a bail wire coupled to the cap by ends of the bail wire in bores of the cap. The articulating step includes articulating an extension arm coupled by a hinge pin to the cap to push a male connector of a second medical device through the procedural barrier and into a female connector of the first medical device. The functional connection-establishing step includes establishing one or more functional connections across the procedural barrier between the second medical device on a clinician-facing side of the procedural barrier and the first medical device on a patient-facing side of the procedural barrier.

These and other features of the concepts provided herein will become more apparent to those of skill in the art in view of the accompanying drawings and following description, which describe particular embodiments of such concepts in greater detail.

DRAWINGS

DESCRIPTION

Figure 1:
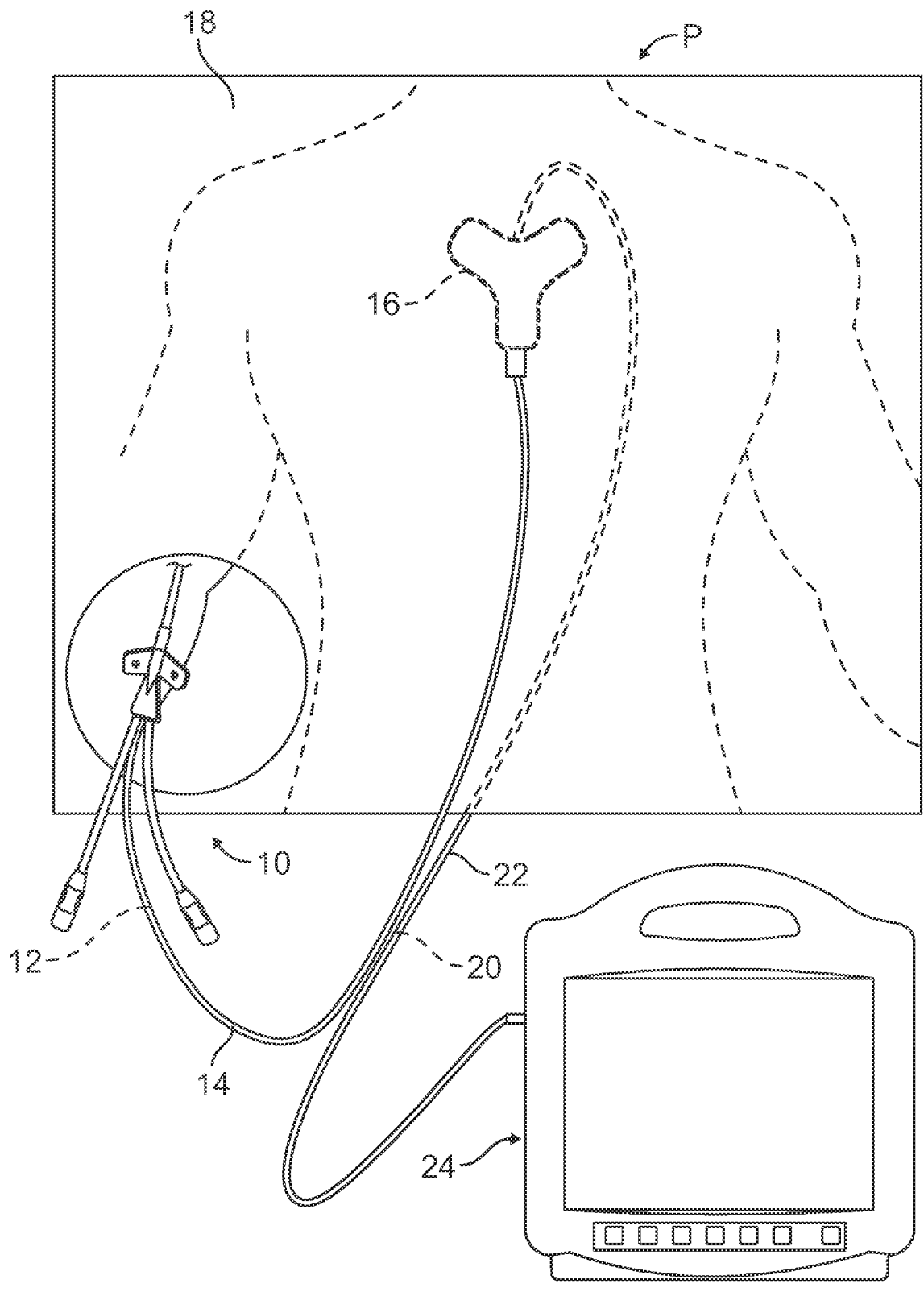
FIG. 1 illustrates functionally connected single-use and multiple-use medical devices of an optical shape-sensing system in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

FIG. 1 illustrates functionally connected single-use and multiple-use medical devices of an optical shape-sensing system in accordance with some embodiments.

As set forth above, medical procedures often require multiple-use medical devices that cannot be sterilized, which mandate placement of such medical devices under sterile drapes; however, sterile single-use medical devices often need to be functionally connected to the multiple-use medical devices. Indeed, as shown, the optical shape-sensing system of FIG. 1 includes a single-use peripherally inserted central catheter ("PICC") 10 having an optical-fiber stylet 12 disposed in an extension tube 14 functionally connected to a relay module 16 over a patient P but under a sterile drape 18 outside of a sterile field. The relay module 16, in turn, includes an optical fiber 20 disposed in a patch cable 22 functionally connected to a console 24 or an optical interrogator thereof that is also outside of the sterile field. Again, some existing solutions rely on arbitrarily breaching sterile drapes (e.g., the sterile drape 18) to make functional connections between sterile single-use medical devices (e.g., the PICC 10) and multiple-use medical devices (e.g., the relay module 16, the console 24, etc.). But arbitrarily breaching such sterile drapes risks contaminating the sterile fields carefully established about the patients. That, and establishing some functional connections such as optical connections between the sterile single-use medical devices and the multiple-use medical devices can be difficult, particularly through arbitrary, self-made breaches in the sterile drapes. What is needed are procedural barrier-breaching connectors and connection-establishing devices for establishing safe, routine, functional connections between sterile single-use medical devices and multiple-use medical devices.

Disclosed herein are procedural barrier-breaching connectors and connection-establishing devices, as well as systems and methods thereof, for establishing portals in procedural barriers.

Figure 2:
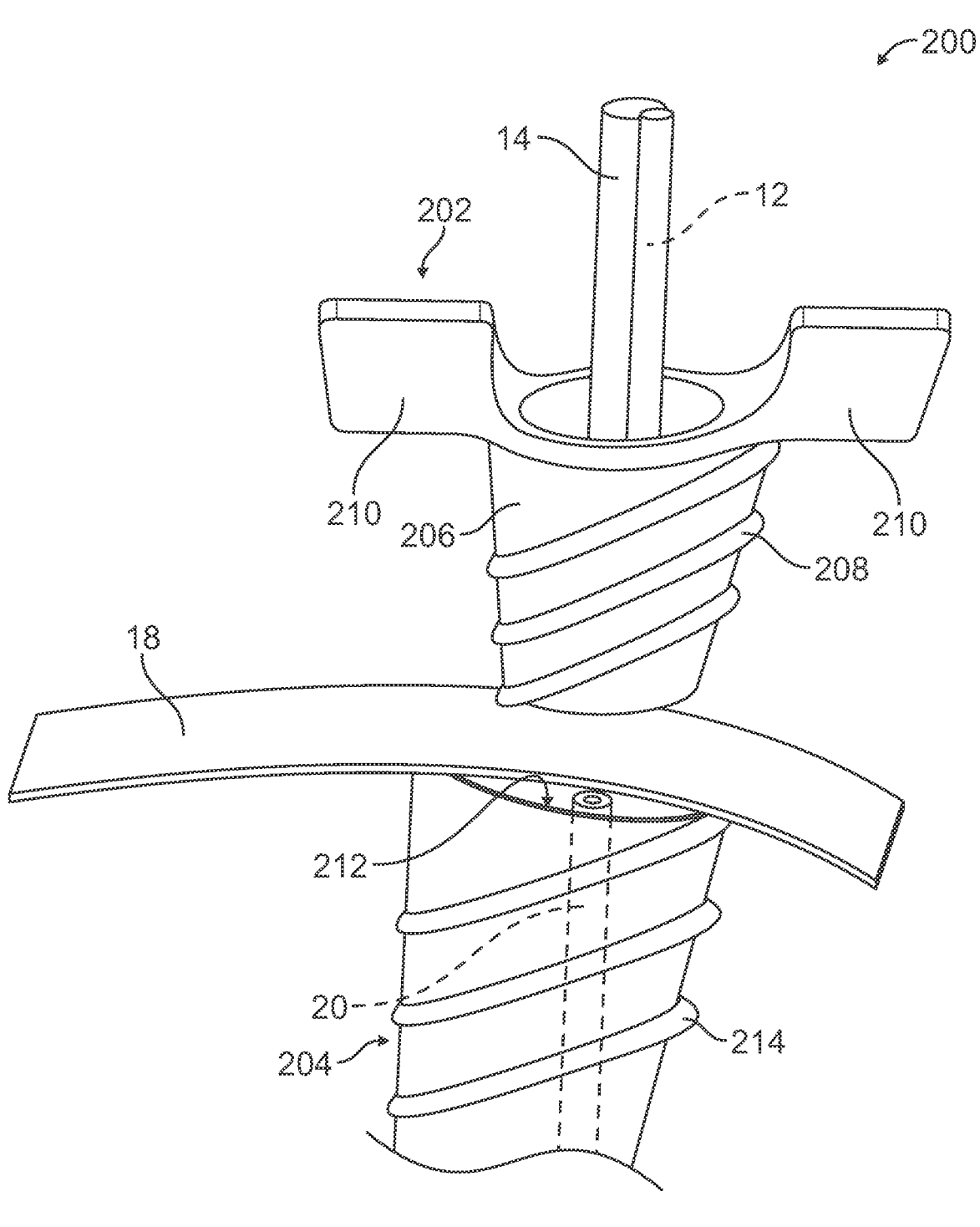
FIG. 2 illustrates a first connection system in accordance with some embodiments.

FIG. 2 illustrates a first connection system 200 in accordance with some embodiments.

As shown the connection system 200 includes a male connector 202 and a female connector 204.

The male connector includes a base 206, external threads 208 around the base 206, and opposing wings 210 about a portion of the base 206. The base 206 includes a longitudinal through hole having a terminal opening configured for holding therein a ferrule including an optical fiber such as the optical fiber of the optical-fiber stylet 12 as shown. The external threads 208 around the base 206 of the male connector 202 include a cutting edge configured to cut through a procedural barrier such as the sterile drape 18 when the male connector 202 is held against the procedural barrier and turned by hand along a longitudinal axis thereof, for example, when pressed into the receptacle 212 of the female connector 204 with the procedural barrier therebetween. The wings 210 are opposite the terminal opening. The wings 210 are configured for turning the male connector 202 by hand along the longitudinal axis thereof.

The female connector 204 includes a receptacle 212 and internal threads 214 around the receptacle 212. The receptacle 212 includes a longitudinal through hole having an internal opening (e.g., into the relay 16) configured for holding therein another ferrule including another optical fiber such as the optical fiber 20. The receptacle 212 of the female connector 204 and the base 206 of the male connector 202 are complementarily tapered. In addition, the internal threads 214 around the receptacle 212 are complementary with the external threads 208 of the male connector 202.

The male and female connectors 202 and 204 are configured to establish an optical connection between the optical fiber of the male connector 202 and the other optical fiber of the female connector 204 when the optical fiber and the other optical fiber are respectively held in the male connector 202 and the female connector 204.

The external threads 208 around the base 206 of the male connector 202 and the internal threads 214 around the receptacle 212 of the female connector 204 are electrically conductive. The male and female connectors 202 and 204 are configured to establish an electrical connection between a conductive wire of the male connector 202 and another conductive wire of the female connector 204 when the conductive wire and the other conductive wire are respectively held in the male connector 202 and the female connector 204 and connected to the external threads 208 and the internal threads 214.

Figures 3, 4:
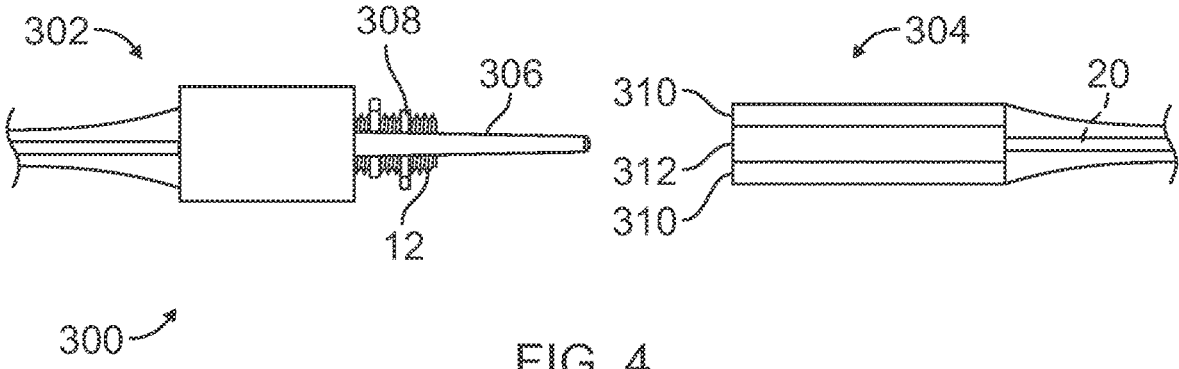
FIG. 3 illustrates a first view of a second connection system in accordance with some embodiments.
FIG. 4 illustrates a second view of the second connection system in accordance with some embodiments.

FIGS. 3 and 4 illustrate different views of a second connection system 300 in accordance with some embodiments.

As shown, the connection system 300 includes a male connector 302 and a female connector 304.

The male connector 302 includes two or more prongs 306 and an optical-fiber holder 308. The two-or-more prongs 306 extend to a common terminal end of the male connector 302. Each prong of the two-or-more prongs 306 of the male connector 302 includes a cutting edge configured to cut through a procedural barrier such as the sterile drape 18 when the male connector 302 is held against the procedural barrier and pushed by hand therethrough, for example, when pressed into the two-or-more prong receptacles 310 of the female connector 304 with the procedural barrier therebetween. The optical-fiber holder 308 is along a longitudinal axis of the male connector 302 between the two-or-more prongs 306 and short of the common terminal end. The optical-fiber holder 306 is configured for holding therein a ferrule including an optical fiber such as the optical fiber of the optical-fiber stylet 12 as shown.

The female connector 302 includes two or more prong receptacles 310 and an optical-fiber receptacle 312. The two-or-more prong receptacles 310 correspond in number to the two-or-more prongs 306 and extend to a common terminal end of the female connector 304. The optical-fiber receptacle 312 is along a longitudinal axis of the female connector 304 between the two-or-more prong receptacles 310 and commensurate with the common terminal end of the female connector 304. The optical-fiber receptacle 312 is configured for holding therein another ferrule including another optical fiber such as the optical fiber 20.

The male and female connectors 302 and 304 are configured to establish an optical connection between the optical fiber of the male connector 302 and the other optical fiber of the female connector 304 when the optical fiber and the other optical fiber are respectively held in the male connector 302 and the female connector 304.

The two-or-more prongs 306 of the male connector 302 and two or more contacts respectively disposed within the two-or-more prong receptacles 310 of the female connector 304 are electrically conductive. The male and female connectors 302 and 304 are configured to establish an electrical connection between a conductive wire of the male connector 302 and another conductive wire of the female connector 304 when the conductive wire and the other conductive wire are respectively coupled to the two-or-more prongs 306 in the male connector 302 and the two-or-more contacts in female connector 304.

Figures 5, 6:
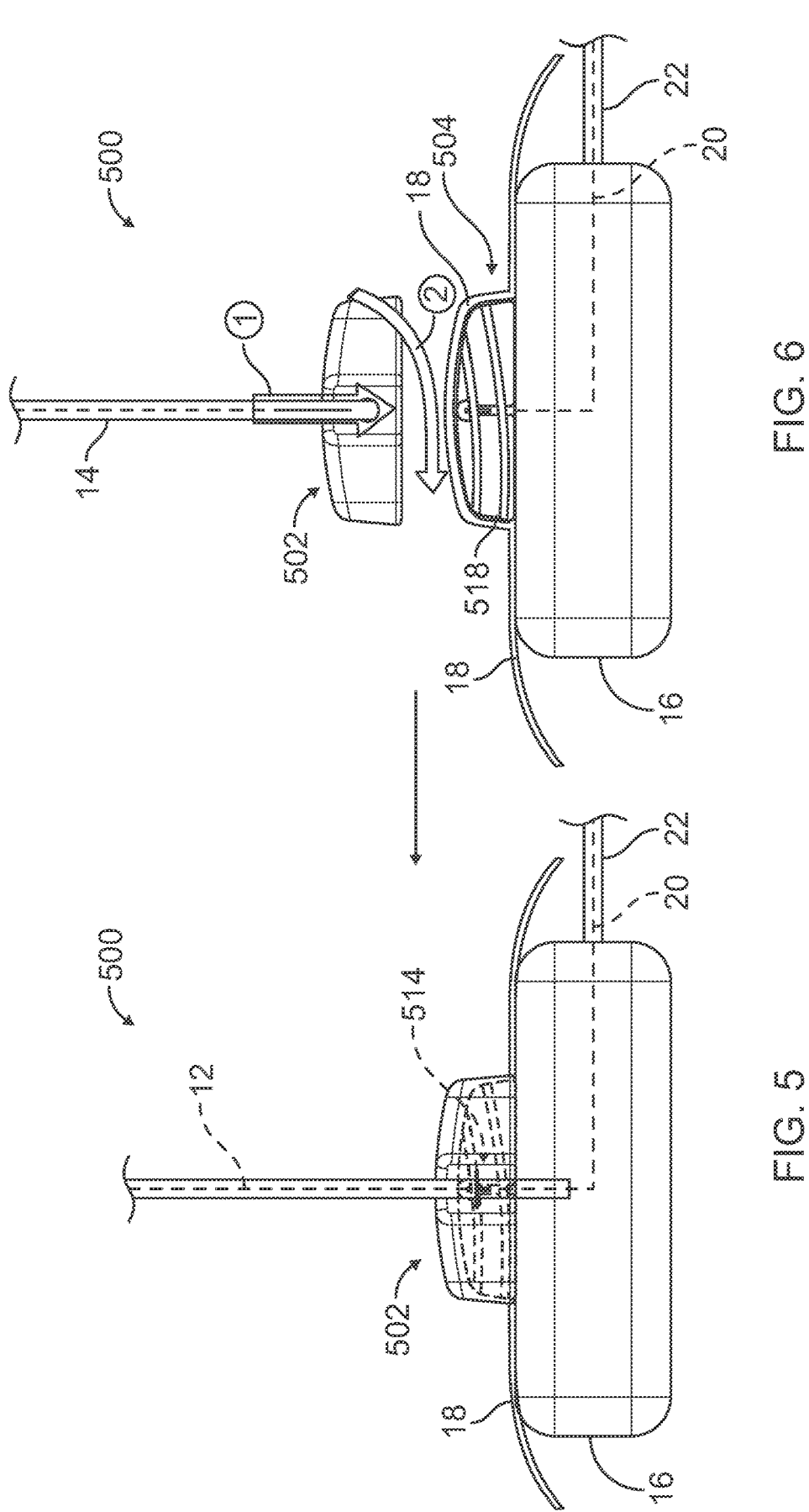
FIG. 5 illustrates a first view of a third connection system in accordance with some embodiments.
FIG. 6 illustrates a second view of the third connection system in accordance with some embodiments.
Figures 7, 8:
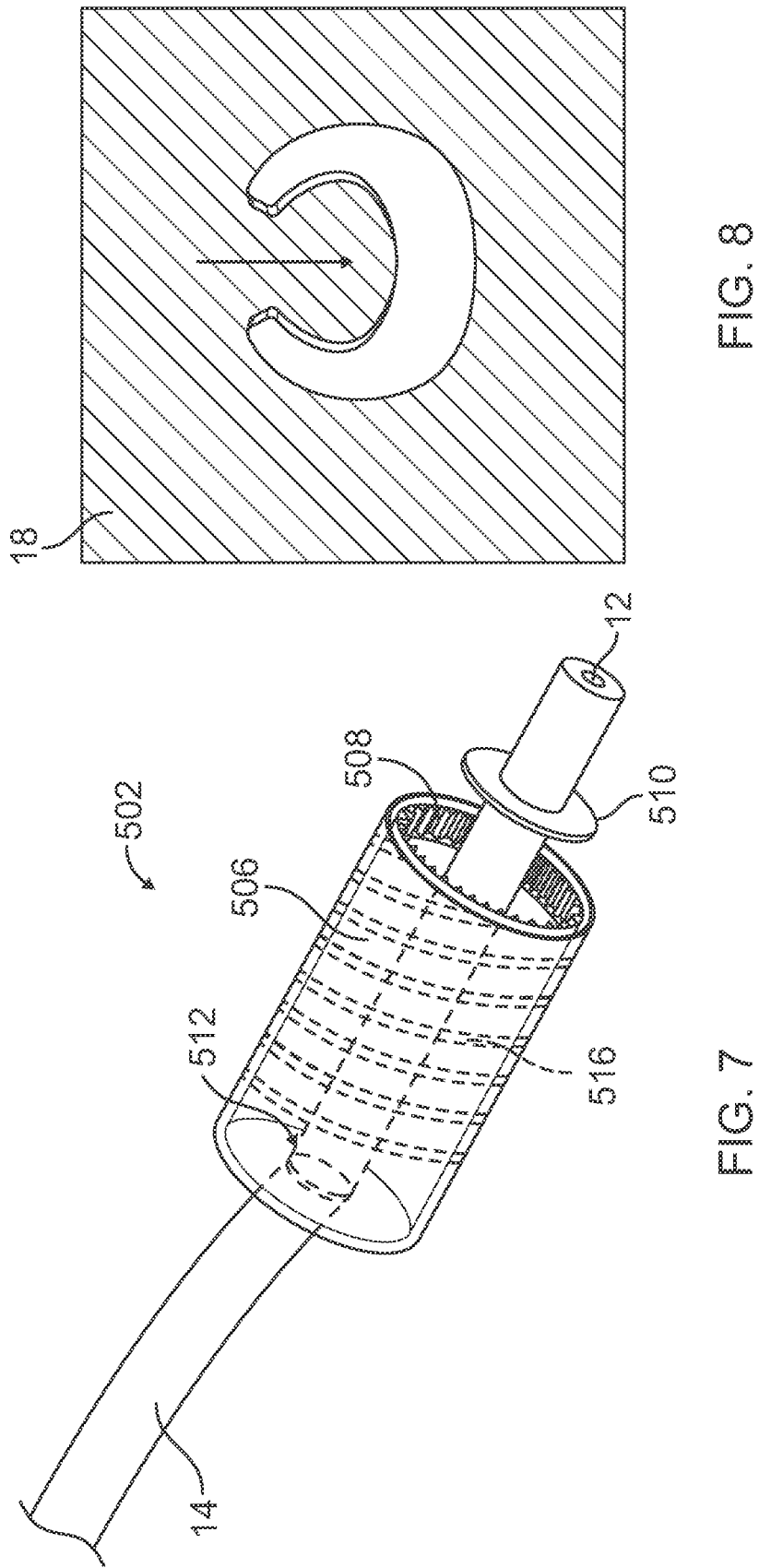
FIG. 7 illustrates a male connector of the third connection system in accordance with some embodiments.
FIG. 8 illustrates a breach in a procedural barrier when breached by the male connector of FIG. 5 in accordance with some embodiments.

FIGS. 5 and 6 illustrate different views of the third connection system 500 in accordance with some embodiments. FIG. 7 illustrates a male connector 502 of the third connection system 500 in accordance with some embodiments. FIG. 8 illustrates a breach in a procedural barrier such as the sterile barrier 18 when breached by the male connector 502 of FIG. 7 in accordance with some embodiments. It should be understood that while the male connector 502 of FIGS. 5 and 6 appears different than that of FIG. 7, the male connector 502 can be in any form complementary to the female connector 504 set forth below.

As shown, the connection system 500 includes the male connector 502 and a female connector 504.

The male connector 502 includes a sleeve 506, a cutting edge 508 around a major opening of the sleeve 506, and a holed stopper 510 (e.g., an 'O'-ring). The sleeve 506 has a through hole 512 configured to allow a cable (e.g., the extension tube 14) including an optical fiber (e.g., the optical fiber of the optical-fiber stylet 12) to be slidably disposed therein for sliding the cable into the sleeve 506 for cutting through a procedural barrier (e.g., the sterile drape 18) or out of the major opening at a terminal end of the male connector 502 and through a hole cut in the procedural drape (see FIG. 8) for making at least an optical connection. The cutting edge 508 is opposite the through hole 512. The cutting edge 508 is configured to cut through the procedural barrier when the sleeve 506 is held against the procedural barrier and turned by hand along a longitudinal axis of the sleeve 506. Notably, the through hole 512 of the sleeve 506 is also configured to allow the cable to be rotatably disposed therein for turning the sleeve 506 and cutting through the procedural barrier with the cutting edge 508 without twisting the cable. The holed stopper 510 is configured to be disposed over the cable or a ferrule around the optical fiber to stop the cable from slipping though the through hole when sliding the cable into the sleeve 506 for cutting through a procedural barrier.

The female connector 504 includes an optical-fiber receptacle 514. The optical-fiber receptacle 514 includes a longitudinal through hole having an internal opening configured for holding therein another ferrule including another optical fiber such as the optical fiber 20.

The male and female connectors 502 and 504 are configured to establish an optical connection between the optical fiber of the male connector 502 and the other optical fiber of the female connector 504 when the optical fiber and the other optical fiber are respectively held in the male connector 502 and the female connector 504.

Optionally, the male connector 502 and the female connector 504 can include complementary threads. Indeed, the sleeve 506 of the male connector 502 can have internal threads 516 around an inside of the sleeve 506 and the female connector 504 can have complementary external threads 518 around an outside of the optical-fiber receptacle 514. The internal threads 516 of the male connector 502 and the external threads 518 of the female connector 504 are configured for screwing together the male connector 502 and the female connector 504.

Figures 9, 10:
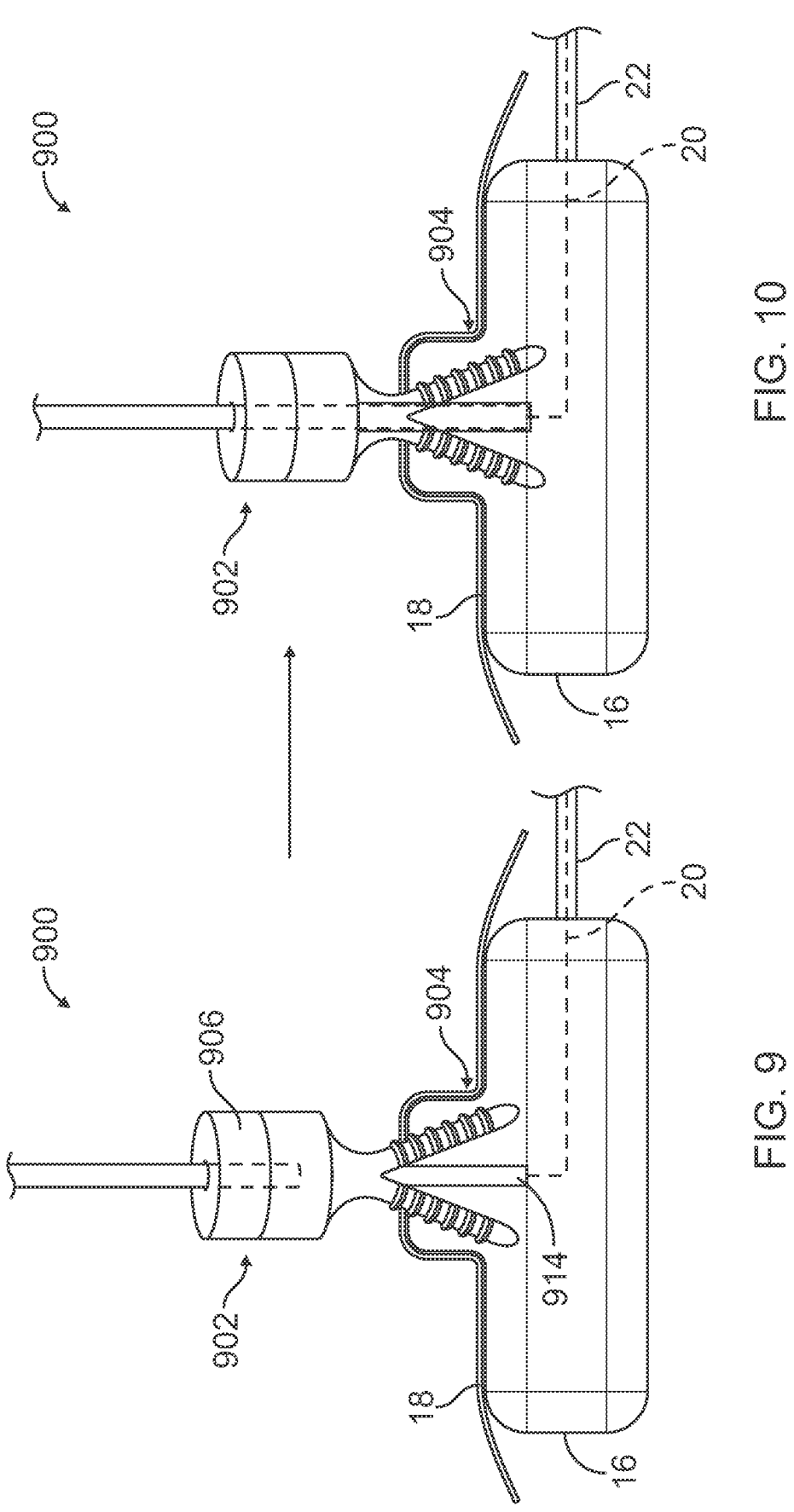
FIG. 9 illustrates a first view of a fourth connection system in accordance with some embodiments.
FIG. 10 illustrates a second view of the fourth connection system in accordance with some embodiments.
Figure 11:
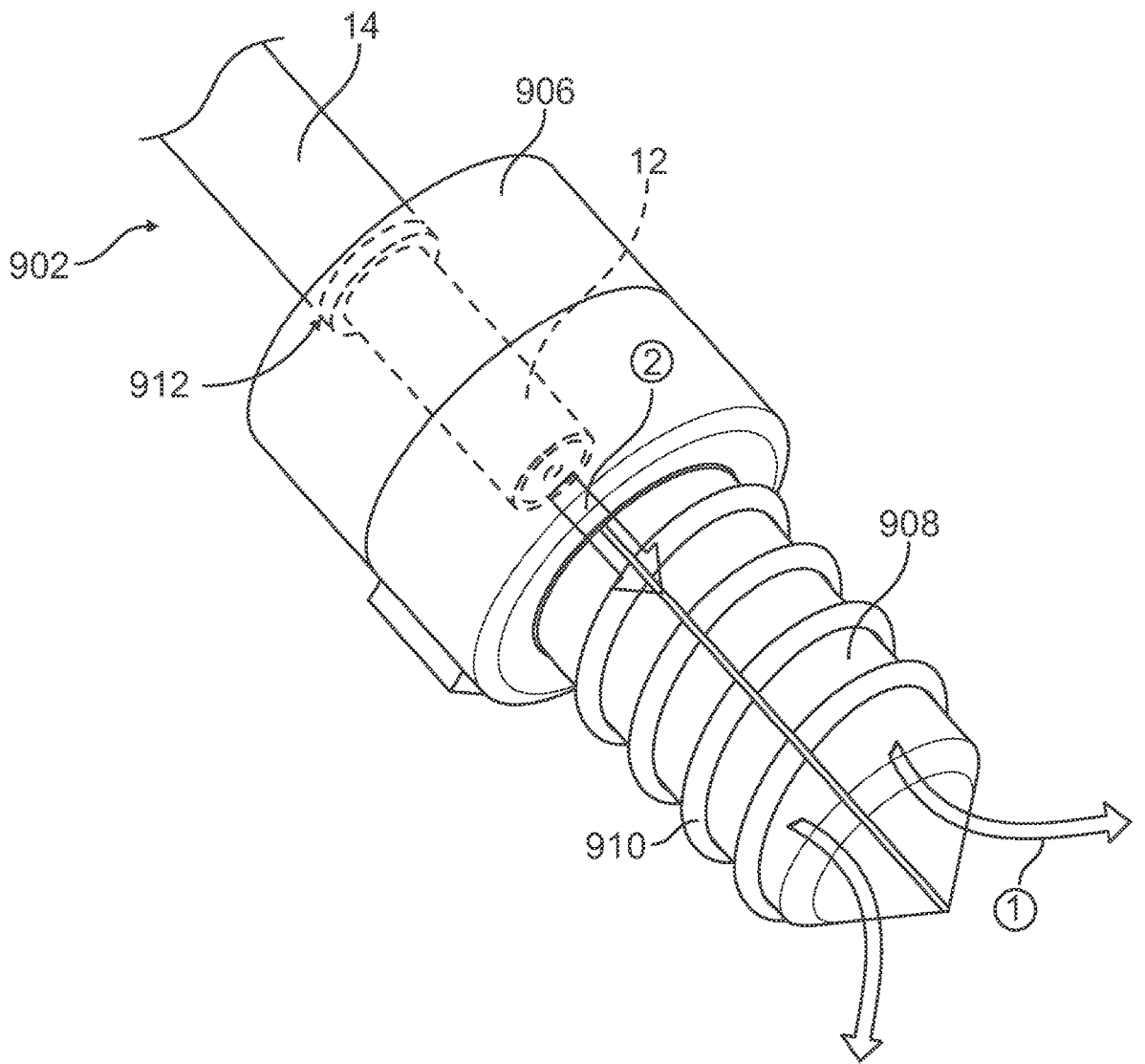
FIG. 11 illustrates a male connector of the fourth connection system in accordance with some embodiments.

FIGS. 9 and 10 illustrate different views of a fourth connection system 900 in accordance with some embodiments. FIG. 9 illustrates a male connector 902 of the fourth connection system 900 in accordance with some embodiments.

As shown, the connection system 900 includes the male connector 902 and a female connector 904.

The male connector 902 includes a head 906, a splittable shank 908 extending from the head 906, and a spiral cutting edge 910 around the splittable shank 908. The head 906 has a through hole 912 configured to allow a cable (e.g., the extension tube 14) including an optical fiber (e.g., the optical fiber of the optical-fiber stylet 12) to be slidably disposed therein for sliding the cable out of the splittable shank 908 for making at least an optical connection. The splittable shank 908 is configured to split along its length to allow a ferrule including the optical fiber of the cable to be pushed past a terminal end of the male connector 902. The spiral cutting edge 910 is configured to cut through a procedural barrier (e.g., the sterile drape 18) when the male connector 902 is held against the procedural barrier and turned by hand along the longitudinal axis thereof.

The female connector 904 includes an optical-fiber receptacle 914. The optical-fiber receptacle 914 includes a longitudinal through hole having an internal opening configured for holding therein another ferrule including another optical fiber (e.g., the optical fiber 20). The optical-fiber receptacle 914 is configured to split the splittable shank 908 when the splittable shank 908 is inserted therein, which, in turn, allows the ferrule including the optical fiber of the cable to be pushed past the terminal end of the male connector 902 to establish at least an optical connection with the female connector 904. Indeed, the male and female connectors 902 and 904 are configured to establish an optical connection between the optical fiber of the male connector 902 and the other optical fiber of the female connector 904 when the optical fiber and the other optical fiber are respectively held in the male connector 902 and the female connector 904.

Figure 12:
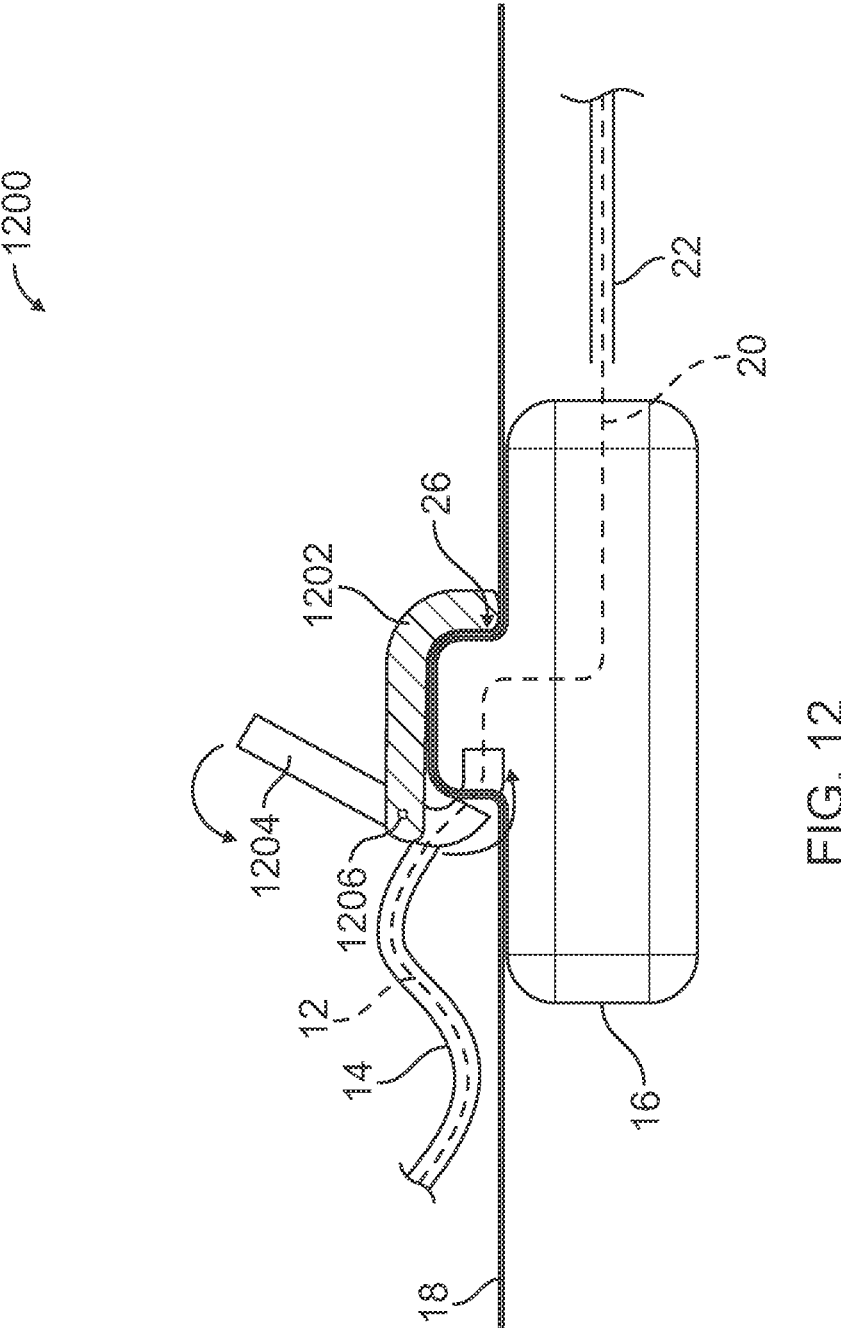
FIG. 12 illustrates a first connection-establishing device in accordance with some embodiments.
Figure 13:
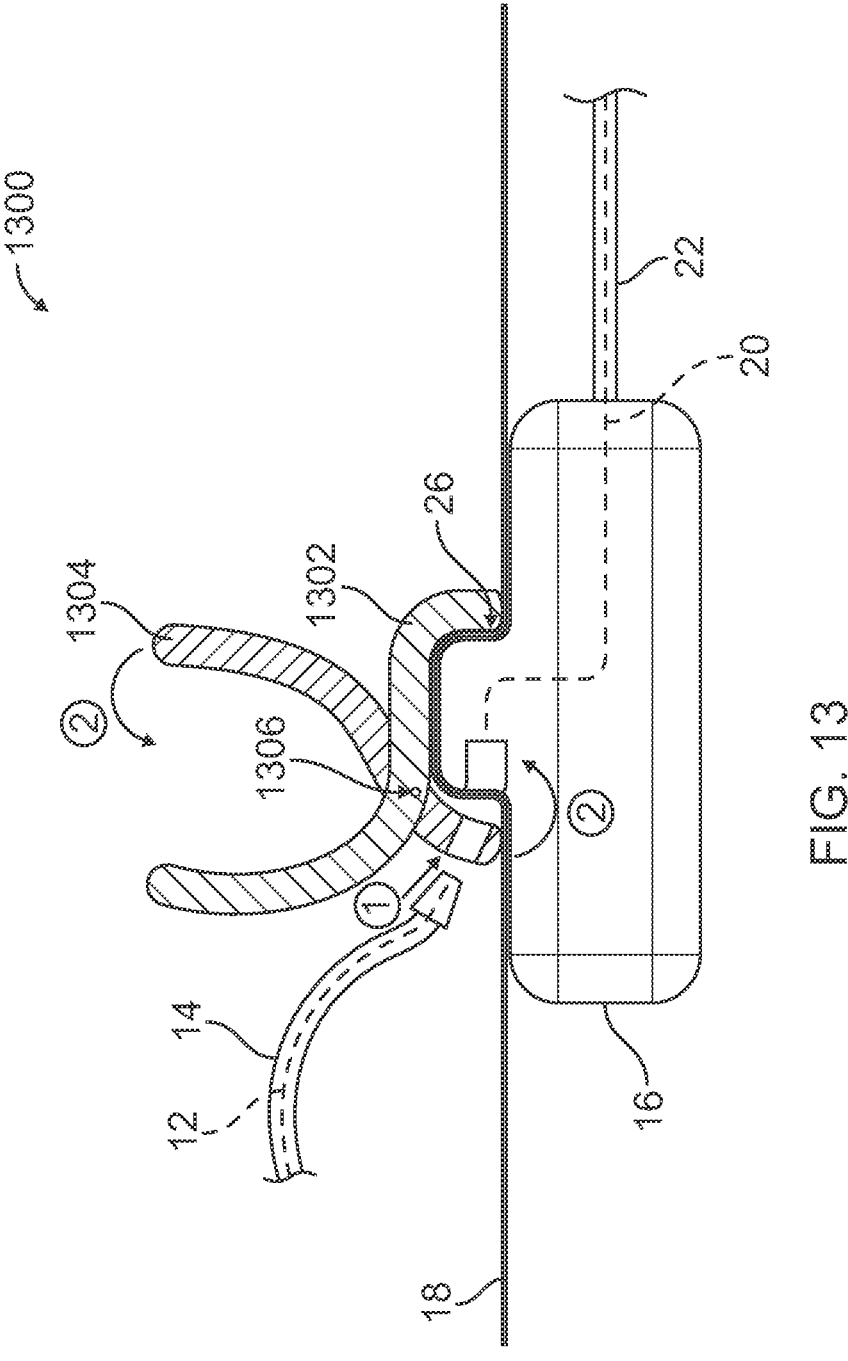
FIG. 13 illustrates a second connection-establishing device in accordance with some embodiments.
Figure 14:
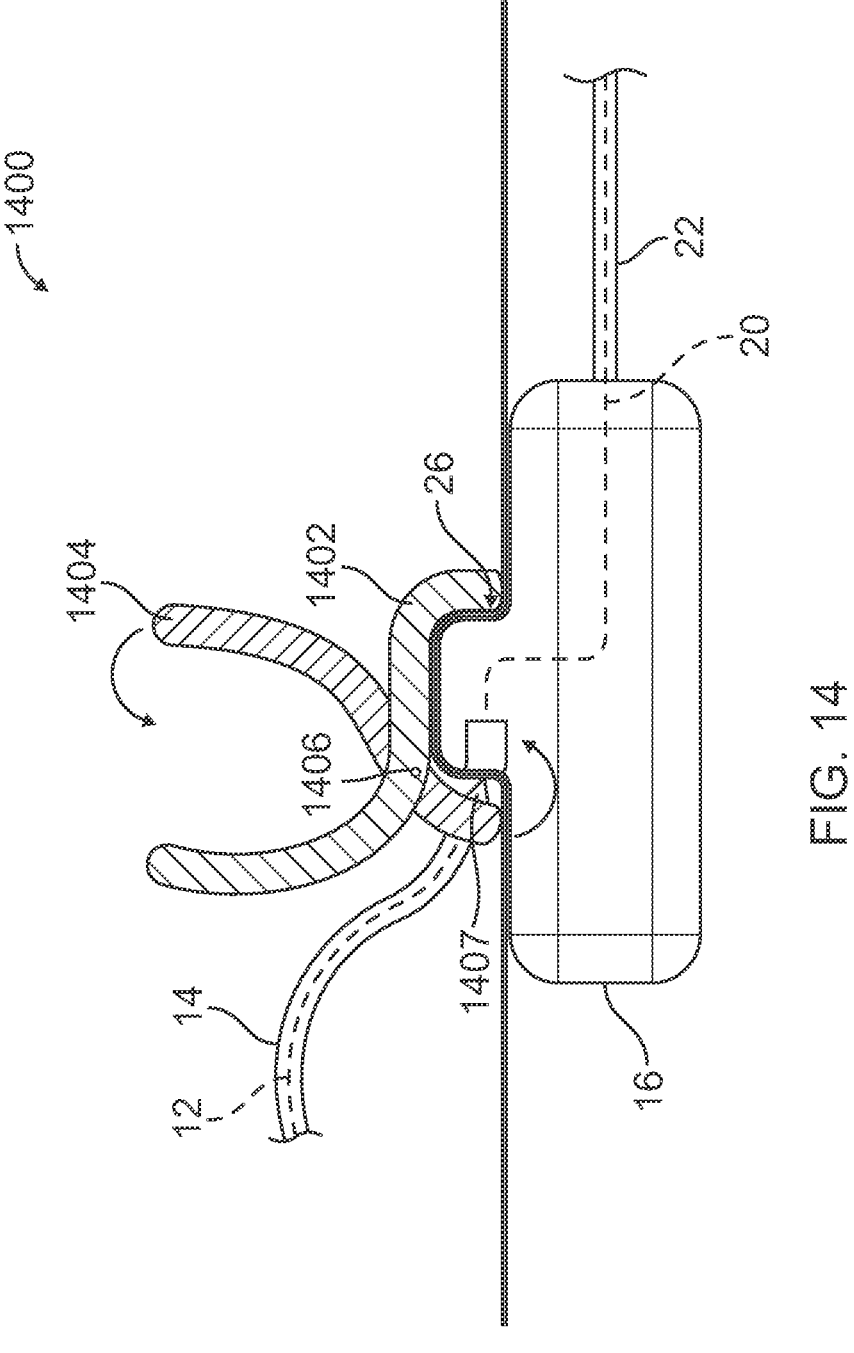
FIG. 14 illustrates a third connection-establishing device in accordance with some embodiments.

FIGS. 12, 13, and 14 respectively illustrate a first connection-establishing device 1200, a second connection-establishing device 1300, and a third connection-establishing device 1400 in accordance with some embodiments.

As shown, the connection-establishing device 1200, 1300, or 1400 includes a cap 1202, 1302, or 1402 and an extension arm 1204, 1304, or 1404. The cap 1202, 1302, or 1402 is configured to sit over a protruding portion 26 of, for example, a multiple-use medical device (e.g., the relay module 16) with a procedural barrier (e.g., the sterile drape 18) between the connection-establishing device 1200, 1300, or 1400 and the multiple-use medical device. The extension arm 1204, 1304, or 1404 is coupled by a hinge pin 1206, 1306, or 1406 to the cap 1202, 1302, or 1402. The extension arm 1204 or 1304 is configured to push a male connector (e.g., the male connector 202 or 302) of a single-use medical device (e.g., the PICC 10) through the procedural barrier and into a female connector (e.g., the female connector 204 or 304) of the multiple-use medical device, whereas the extension arm 1404 is configured to push a punch 1407 including an alternative male connector therein through the procedural barrier and into an alternative female connector. Regardless, by articulating the extension arm extension arm 1204, 1304, or 1404, one or more functional connections (e.g., an optical connection, an electrical connection, or an optical connection and an electrical connection) are established across the procedural barrier between the single-use medical device on a clinician-facing side of the procedural barrier and the multiple-use medical device on a patient-facing side of the procedural barrier.

Advantageously, the connection-establishing device 1200, 1300, or 1400 utilizes a mechanical advantage to decrease the force required to make the one-or-more functional connections through the procedural barrier.

Figure 15:
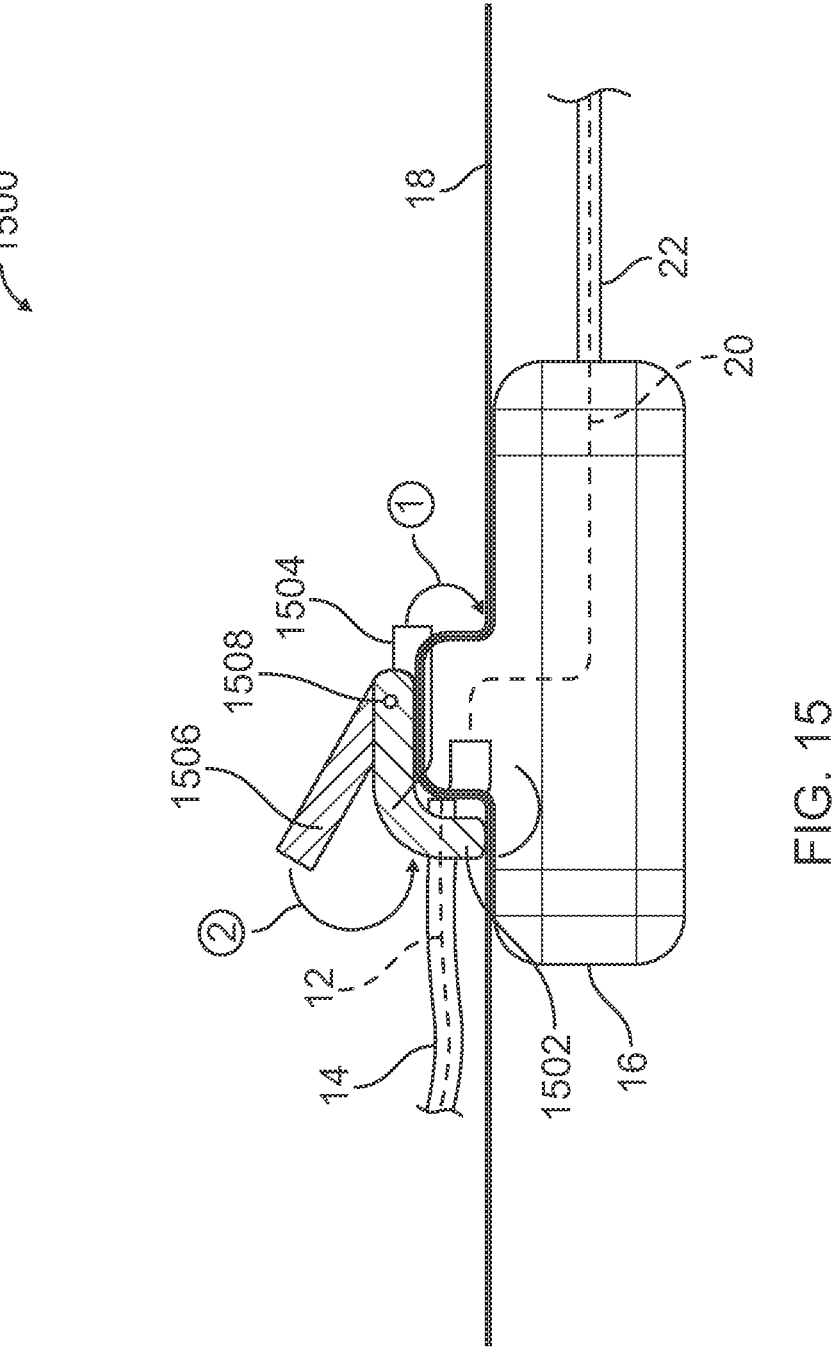
FIG. 15 illustrates a fourth connection-establishing device in accordance with some embodiments.

FIG. 15 illustrates a fourth connection-establishing device 1500 in accordance with some embodiments.

As shown, the connection-establishing device 1500 includes a cap 1502, bail wire 1504 coupled to the cap 15002, and an extension arm 1506 coupled to the cap 1502. The cap 1502 is configured to sit over the protruding portion 26 of, for example, the multiple-use medical device set forth above with the same procedural barrier between the connection-establishing device 1500 and the multiple-use medical device. The bail wire 1504 is coupled to the cap 1502 by ends of the bail wire 1504 in bores of the cap 1502. The bail wire 1504 is configured to secure the cap 1502 over the protruding portion 26 of the medical device by way of a hinge mechanism. The extension arm 1506 is coupled by a hinge pin 1508 to the cap 1502. The extension arm 1506 is configured to push a male connector (e.g., the male connector 202 or 302) of a single-use medical device (e.g., the PICC 10) through the procedural barrier and into a female connector (e.g., the female connector 204 or 304) of the multiple-use medical device by articulating the extension arm 1506. The extension arm 1506 is thusly configured to establish one or more functional connections (e.g., an optical connection, an electrical connection, or an optical connection and an electrical connection) across the procedural barrier between the single-use medical device on a clinician-facing side of the procedural barrier and the multiple-use medical device on a patient-facing side of the procedural barrier.

Advantageously, the connection-establishing device 1500 utilizes a mechanical advantage to decrease the force required to make the one-or-more functional connections through the procedural barrier.

Methods

Methods include methods of using the procedural barrier-breaching connectors and the connection-establishing devices set forth above, as well as the systems thereof.

Adverting to FIG. 2, which illustrates the first connection system 200 in accordance with some embodiments, a method of the connection system 200 includes a connector-placing step, a connector-turning step, and optical connection-establishing step.

The connector-placing step includes placing a bottom portion of the base 206 of the male connector 202 into a top portion of the receptacle 212 of the female connector 204 with a procedural barrier (e.g., the sterile drape 18) therebetween.

The connector-turning step includes turning the male connector 204 by hand along a longitudinal axis thereof by way of the opposing wings 210 about a portion of the base 206 opposite the bottom portion of the base 206 while placing the male connector 202 against the procedural drape. The connector-turning step also includes cutting through the procedural barrier with the external threads 208 around the base 206 of the male connector 204 having the cutting edge.

The optical connection-establishing step includes establishing an optical connection between an optical fiber (e.g., the optical fiber of the optical-fiber stylet 12) disposed in the terminal opening in the bottom portion of the male connector 202 and another optical fiber (e.g., the optical fiber 20) disposed in the internal opening of the female connector 204 respectively held in the male connector 202 and the female connector 204.

The method can further include an electrical connection-establishing step. The electrical connection-establishing step includes establishing an electrical connection between a conductive wire of the male connector 202 and another conductive wire of the female connector 204. The conductive wire and the other conductive wire are respectively connected to the external threads 208 of the male connector 202 and the complementary internal threads 214 around the receptacle 212 of the female connector 204.

Adverting to FIGS. 3 and 4, which illustrate different views of the second connection system 300 in accordance with some embodiments, a method of the connection system 300 includes a connector-placing step, a connector-pushing step, and an optical connection-establishing step.

The connector-placing step includes placing the two-or-more prongs 306 of the male connector 302 against a procedural barrier (e.g., the sterile drape 18).

The connector-pushing step includes pushing the two-or-more prongs 306 through the procedural barrier into the two-or-more prong receptacles 310 of the female connector 304 corresponding in number to the two-or-more prongs 306 of the male connector 302. The connector-pushing step also includes cutting through the procedural barrier with the cutting edge of each prong of the two-or-more prongs 306 of the male connector 302.

The optical connection-establishing step includes establishing an optical connection between an optical fiber (e.g., the optical fiber of the optical-fiber stylet 12) disposed in the optical-fiber holder 308 along the longitudinal axis of the male connector 302 between the two-or-more prongs 306 and another optical fiber (e.g., the optical fiber 20) disposed in the optical-fiber receptacle 312 along the longitudinal axis of the female connector 304 between the two-or-more prong receptacles 310.

The method can further include an electrical connection-establishing step. The electrical connection-establishing step includes establishing an electrical connection between a conductive wire coupled to the two-or-more prongs 306 of the male connector 302 and another conductive wire coupled to the two-or-more contacts respectively disposed within the two-or-more prong receptacles 310 of the female connector 304.

Again, FIGS. 5 and 6 illustrate different views of the third connection system 500 in accordance with some embodiments; FIG. 7 illustrates the male connector 502 of the third connection system 500 in accordance with some embodiments; and FIG. 8 illustrates a breach in a procedural barrier when breached by the male connector 502 of FIG. 7 in accordance with some embodiments. A method of the connection system 500 includes a connector-placing step, a connector-turning step, and a cable-sliding step.

The connector-placing step includes placing a bottom portion of the sleeve 506 of the male connector 502 over a top portion of the optical-fiber receptacle 514 of the female connector 504 with a procedural barrier therebetween (e.g., the sterile drape 18).

The connector-turning step includes turning the male connector 502 by hand along the longitudinal axis of the sleeve 506 while placing the male connector 502 against the procedural drape. The connector-turning step also includes cutting through the procedural barrier with the cutting edge 508 around the major opening of the sleeve 506 opposite the through hole. As set forth above, the sleeve 506 of the male connector 502 has the internal threads 516 around the inside of the sleeve 506 and the female connector 504 has the complementary external threads 518 around the outside of the receptacle 514. As such, the connector-turning step can also include screwing together the male connector 502 and the female connector 504 subsequent to cutting the procedural drape in the foregoing sub-steps of the connector-turning step.

The cable-sliding step includes sliding a cable (e.g., the extension tube 14) including an optical fiber (e.g., the optical fiber of the optical-fiber stylet 12) through the through hole 512 opposite the bottom portion of the sleeve 506 of the male connector 502 into the receptacle 514 of the female connector 504. The cable-sliding step also includes establishing an optical connection between the optical fiber and another optical fiber (e.g., the optical fiber 20) disposed in the receptacle 514 of the female connector 504.

Again, FIGS. 9 and 10 illustrate different views of the fourth connection system 900 in accordance with some embodiments; and FIG. 9 illustrates the male connector 902 of the fourth connection system 900 in accordance with some embodiments. A method of the connection system 900 includes a connector-placing step, a connector-turning step, a connector-inserting step, and a cable-sliding step.

The connector-placing step includes placing the spiral cutting edge 910 of the splittable shank 908 of the male connector 902 over the longitudinal through hole of the optical-fiber receptacle 914 of the female connector 904 with a procedural barrier (e.g., the sterile drape 18) therebetween. The connector-turning step also includes turning the male connector 902 by hand along the longitudinal axis thereof while placing the male connector 902 against the procedural drape. The connector-turning step also includes cutting through the procedural barrier with the cutting edge 910 of the splittable shank 908.

The connector-inserting step includes inserting the splittable shank 908 into the longitudinal through hole of the receptacle 914 of the female connector 904 and splitting the splittable shank 908 along its length.

The cable-sliding step includes sliding a cable (e.g., the extension tube 14) including an optical fiber (e.g., the optical fiber of the optical-fiber stylet 12) through the through hole in the head 906 of the male connector 902 opposite the splittable shank 908 into the receptacle 914 of the female connector 904. The cable-sliding step also includes establishing an optical connection between the optical fiber and another optical fiber (e.g., the optical fiber 10) disposed in the receptacle 914 of the female connector 904.

Adverting to FIGS. 12, 13, and 14, which respectively illustrate a first connection-establishing device 1200, a second connection-establishing device 1300, and a third connection-establishing device 1400 in accordance with some embodiments, a method of the connection-establishing device 1200, 1300, or 1400 includes a cap-placing step, an articulating step, and a functional connection-establishing step.

The cap-placing step includes placing the cap 1202, 1302, or 1402 over the protruding portion 26 of, for example, a multiple-use medical device (e.g., the relay module 16) with a procedural barrier (e.g., the sterile drape 18) between the connection-establishing device 1200, 1300, or 1400 and the multiple-use medical device.

The articulating step includes articulating the extension arm 1204, 1304, or 1404 coupled by the hinge pin 1206, 1306, or 1406 to the cap 1202, 1302, or 1402 to push a male connector (e.g., the male connector 202 or 302) of a single-use medical device (e.g., the PICC 10) through the procedural barrier and into a female connector (e.g., the female connector 204 or 304) of the multiple-use medical device.

The functional connection-establishing step includes establishing one or more functional connections (e.g., an optical connection, an electrical connection, or an optical connection and an electrical connection) across the procedural barrier between the single-use medical device on a clinician-facing side of the procedural barrier and a multiple-use medical device on a patient-facing side of the procedural barrier.

Adverting to FIG. 15, which illustrates the fourth connection-establishing device 1500 in accordance with some embodiments, a method of the connection-establishing device includes a cap-placing step, a securing step, an articulating step, and a functional connection-establishing step.

The cap-placing step includes placing the cap 1502 over the protruding portion 26 of, for example, a multiple-use medical device (e.g., the relay module 16) with a procedural barrier (e.g., the sterile drape 18) between the connection-establishing device 1500 and the multiple-use medical device.

The securing step includes securing the cap 1502 over the protruding portion 26 of the medical device by way of a hinge mechanism of the bail wire 1504 coupled to the cap 1502 by ends of the bail wire 1504 in bores of the cap 1502.

The articulating step includes articulating the extension arm 1506 coupled by the hinge pin 1508 to the cap 1502 to push a male connector (e.g., the male connector 202 or 302) of a single-use medical device (e.g., the PICC 10) through the procedural barrier and into a female connector (e.g., the female connector 204 or 304) of the multiple-use medical device.

The functional connection-establishing step includes establishing one or more functional connections across the procedural barrier between the single-use medical device on a clinician-facing side of the procedural barrier and a multiple-use medical device on a patient-facing side of the procedural barrier.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A connection system, comprising:
a male connector including:
  a base including a longitudinal through hole having a terminal opening configured for holding therein a ferrule including an optical fiber;
  external threads around the base; and
  opposing wings about a portion of the base opposite the terminal opening configured for turning the male connector by hand along a longitudinal axis thereof; and a female connector including:
  a receptacle including a longitudinal through hole having an internal opening configured for holding therein a second ferrule including a second optical fiber; and
  internal threads around the receptacle complementary with the external threads of the male connector, the male connector and the female connector configured to establish an optical connection between the optical fiber of the male connector and the second optical fiber of the female connector when the optical fiber and the second optical fiber are respectively held in the male connector and the female connector.

2. The connection system of claim 1, wherein the external threads around the base of the male connector and the internal threads around the receptacle of the female connector are electrically conductive, the male connector and the female connector configured to establish an electrical connection between a conductive wire of the male connector and a second conductive wire of the female connector when the conductive wire and a second conductive wire are respectively held in the male connector and the female connector and connected to the internal threads and the external threads.

3. The connection system of claim 1, wherein the external threads around the base of the male connector include a cutting edge configured to cut through a procedural barrier when the male connector is placed against the procedural barrier and turned by hand along the longitudinal axis thereof.

4. The connection system of claim 1, wherein the base of the male connector and the receptacle of the female connector are complementarily tapered.

* * * * *